United States Patent [19]
Dassel et al.

[11] Patent Number: 5,824,819
[45] Date of Patent: Oct. 20, 1998

[54] METHODS OF PREPARING AN INTERMEDIATE OXIDATION PRODUCT FROM A HYDROCARBON BY UTILIZING AN ACTIVATED INITIATOR

[75] Inventors: Mark W. Dassel, Indianola, Wash.; Eustathios Vassiliou, Newark, Del.; David C. DeCoster, Buckley; Ader M. Rostami, Bainbridge Island, both of Wash.

[73] Assignee: Twenty-First Century Research Corporation, Newark, Del.

[21] Appl. No.: 861,176

[22] Filed: May 21, 1997

Related U.S. Application Data

[60] Provisional application No. 60/032,437 Dec. 18, 1996.

[51] Int. Cl.$^6$ .................. C07C 51/245; C07C 51/16; C07C 51/255
[52] U.S. Cl. .............. 562/529; 562/410; 562/412; 562/413; 562/417; 562/531; 562/543
[58] Field of Search .................. 562/410, 412, 562/413, 417, 529, 531, 543

[56] References Cited

U.S. PATENT DOCUMENTS

| | | | |
|---|---|---|---|
| 1,121,532 | 12/1914 | Newberry . | |
| 2,014,044 | 9/1935 | Haswell | 75/17 |
| 2,223,493 | 12/1940 | Loder | 260/537 |
| 2,223,494 | 12/1940 | Loder | 260/586 |
| 2,301,240 | 11/1942 | Baumann et al. | 183/115 |
| 2,439,513 | 4/1948 | Hamblet et al. | 260/533 |
| 2,557,282 | 6/1951 | Hamblet et al. | 260/533 |
| 2,565,087 | 8/1951 | Porter et al. | 260/631 |
| 2,980,523 | 4/1961 | Dille et al. | 48/215 |
| 3,161,603 | 12/1964 | Leyshon et al. | 252/413 |
| 3,231,608 | 1/1966 | Kollar | 260/533 |
| 3,234,271 | 2/1966 | Barker et al. | 260/531 |
| 3,290,369 | 12/1966 | Bonfield et al. | 260/537 |
| 3,361,806 | 1/1968 | Lidov | 260/531 |
| 3,515,751 | 6/1970 | Oberster et al. | 260/533 |
| 3,530,185 | 9/1970 | Pugi | 260/586 |
| 3,613,333 | 10/1971 | Gardenier | 55/89 |
| 3,677,696 | 7/1972 | Bryk et al. | 23/2 |
| 3,839,435 | 10/1974 | Shigeyasu et al. | 260/524 R |
| 3,928,005 | 12/1975 | Laslo | 55/73 |
| 3,932,513 | 1/1976 | Russell | 260/586 |
| 3,946,076 | 3/1976 | Paasen et al. | 260/586 |
| 3,957,876 | 5/1976 | Rapoport et al. | 260/586 |
| 3,987,100 | 10/1976 | Barnette et al. | 260/586 |
| 3,987,808 | 10/1976 | Carbonell et al. | 137/3 |
| 4,039,304 | 8/1977 | Bechthold et al. | 55/10 |
| 4,055,600 | 10/1977 | Langley et al. | 260/586 |
| 4,065,527 | 12/1977 | Graber | 261/79 A |
| 4,308,037 | 12/1981 | Meissner et al. | 55/10 |
| 4,361,965 | 12/1982 | Goumondy et al. | 34/57 |
| 4,370,304 | 1/1983 | Hendriks et al. | 422/224 |
| 4,394,139 | 7/1983 | Board | 55/20 |
| 4,419,184 | 12/1983 | Backlund | 162/49 |
| 4,423,018 | 12/1983 | Lester, Jr. et al. | 423/243 |
| 5,061,453 | 10/1991 | Krippl et al. | 422/106 |
| 5,104,492 | 4/1992 | King et al. | 203/15 |
| 5,123,936 | 6/1992 | Stone et al. | 55/8 |
| 5,170,727 | 12/1992 | Nielsen | 110/346 |
| 5,221,800 | 6/1993 | Park et al. | 562/543 |
| 5,244,603 | 9/1993 | Davis | 261/87 |
| 5,270,019 | 12/1993 | Melton et al. | 422/234 |
| 5,271,904 | 12/1993 | Esposito et al. | 422/105 |
| 5,286,458 | 2/1994 | Yang et al. | 422/168 |
| 5,294,378 | 3/1994 | Succi et al. | 261/130 |
| 5,312,567 | 5/1994 | Kozma et al. | 261/87 |
| 5,321,157 | 6/1994 | Kollar | 562/543 |
| 5,374,767 | 12/1994 | Drinkard et al. | 560/193 |
| 5,396,850 | 3/1995 | Conochie et al. | 110/346 |
| 5,399,750 | 3/1995 | Brun et al. | 562/553 |
| 5,463,119 | 10/1995 | Kollar | 562/543 |
| 5,502,245 | 3/1996 | Dassel et al. | 562/413 |
| 5,558,842 | 9/1996 | Vassiliou et al. | 422/108 |
| 5,580,531 | 12/1996 | Vassiliou et al. | 422/108 |
| 5,654,475 | 8/1997 | Vassiliou et al. | 562/413 |

FOREIGN PATENT DOCUMENTS

| | | | |
|---|---|---|---|
| 0439007A2 | 7/1991 | European Pat. Off. | C07C 68/38 |
| 0751105A2 | 1/1997 | European Pat. Off. | C07B 33/00 |
| 4426132A1 | 1/1996 | Germany . | |
| 45-002374 | 6/1970 | Japan . | |
| 415172 | 8/1934 | United Kingdom | 8132 33 |
| 738808 | 10/1955 | United Kingdom | 2/3 |
| 864106 | 3/1961 | United Kingdom | 2/3 |
| 1143213 | 2/1969 | United Kingdom | 51/16 |
| 2014473 | 8/1979 | United Kingdom | C07B 3/00 |
| WO96/03365 | 2/1996 | WIPO . | |

OTHER PUBLICATIONS

E. Sorribes et al., "Formación de neuvas fases en el proceso de obtención de ácido adípico: causas y efectos que provocan," *Rev. R. Acad. Cienc. Exactas, Fis. Nat. Madrid* (1987), 81(1), 233–5 (+English language translation).

U.S. application No. 08/587,967, Dassel et al., filed Jan 17, 1996.

U.S. application No. 08/812,847, Dassel et al., filed Mar. 6, 1997.

U.S. application No. 08/824,992, Dassel et al., filed Mar. 27, 1997.

U.S. application No. 08/477,195, Dassel et al., filed Jun. 7, 1995.

*Primary Examiner*—Samuel Barts
*Assistant Examiner*—Rosalynd Keys
*Attorney, Agent, or Firm*—Seed and Berry LLP

[57] ABSTRACT

Methods for oxidizing a hydrocarbon to an intermediate oxidation product by utilizing an activated initiator. The initiator is activated by partially oxidizing a first mixture of the initiator and a hydrocarbon, which mixture contains a rather large amount of initiator. The first mixture may even be just initiator. The first mixture, after the partial oxidation, is mixed with a second mixture containing hydrocarbon and a smaller amount of initiator. The second mixture may even contain no initiator at all. The oxidation is continued to a desired degree. Preferably, at least one of the two mixtures, and even more preferably both reaction mixtures contain an oxidation catalyst and an acidic solvent.

46 Claims, 1 Drawing Sheet

METHODS OF PREPARING AN INTERMEDIATE OXIDATION PRODUCT FROM A HYDROCARBON BY UTILIZING AN ACTIVATED INITIATOR

CROSS-REFERENCE TO RELATED APPLICATION

This application claims priority from U.S. Provisional Application No. 60/032,437, filed Dec. 18, 1996, which application is incorporated herein by reference in its entirety.

TECHNICAL FIELD

This invention relates to methods of making intermediate oxidation products, and preferably dibasic acids, such as adipic acid for example, by oxidizing a hydrocarbon, such as cyclohexane for example, with a gas containing an oxidant, preferably oxygen.

BACKGROUND OF THE INVENTION

There is a plethora of references (both patents and literature articles) dealing with the formation of intermediate oxidation products, such as diacids, for example, one of the most important being adipic acid. Adipic acid is used to produce Nylon 66 fibers and resins, polyesters, polyurethanes, and miscellaneous other compounds.

There are different processes of manufacturing intermediate oxidation products, such as adipic acid for example. The conventional process involves a first step of oxidizing cyclohexane with oxygen to a mixture of cyclohexanone and cyclohexanol (KA mixture), and then oxidation of the KA mixture with nitric acid to adipic acid. Other processes include, among others, the "Hydroperoxide Process," the "Boric Acid Process," and the "Direct Synthesis Process," which involves direct oxidation of cyclohexane to adipic acid with oxygen in the presence of solvents, catalysts, and initiators or promoters.

Initiators or promoters are presently being used to shorten considerably an induction period at the beginning of the reaction. Accepted explanations, which have been given regarding the role of the initiators or promoters, involve oxidation of the catalyst, which is usually cobaltous ions to cobaltic ions.

The Direct Synthesis Process has been given attention for a long time. However, to this date it has found little commercial success. One of the reasons is that although it looks very simple at first glance, it is extremely complex in reality. Due to this complexity, one can find strikingly conflicting results, comments, and views in different references.

It is well known that after a reaction has taken place according to the Direct Synthesis, a mixture of two liquid phases is present at ambient temperature, along with a solid phase mainly consisting of adipic acid. The two liquid phases have been called the "Polar Phase" and the "Non-Polar" phase. However, no attention has been paid so far to the importance of the two phases, except for separating the adipic acid from the "Polar Phase" and recycling these phases to the reactor partially or totally with or without further treatment. Further, no attention has been paid to the behavior of catalyst, such as solubility, for example, during reaction conditions.

It is also important to note that most, if not all, studies on the Direct Synthesis Process have been conducted in a batch mode, literally or for all practical purposes.

There is a plethora of references dealing with oxidation of organic compounds to produce acids, such as, for example, adipic acid.

The following references, among the plethora of others, may be considered as representative of oxidation processes relative to the preparation of diacids.

U.S. Pat. No. 5,463,119 (Kollar) discloses a process for the oxidative preparation of $C_5$–$C_8$ aliphatic dibasic acids by
 (1) reacting,
  (a) at least one saturated cycloaliphatic hydrocarbon having from 5 to 8 ring carbon atoms in the liquid phase and
  (b) an excess of oxygen gas or an oxygen-containing gas in the presence of
  (c) a solvent comprising an organic acid containing only primary and/or secondary hydrogen atoms and
  (d) at least about 0.002 mole per 1000 grams of reaction mixture of a polyvalent heavy metal catalyst;
 (2) removing the aliphatic dibasic acid; and
 (3) recycling intermediates, post oxidation components, and derivatives thereof remaining after removal of the aliphatic dibasic acid into the oxidation reaction.

U.S. Pat. No. 5,374,767 (Drinkard et al.) discloses formation of cyclohexyladipates in a staged reactor, e.g., a reactive distillation column. A mixture containing a major amount of benzene and a minor amount of cyclohexene is fed to the lower portion of the reaction zone and adipic acid is fed to the upper portion of the reaction zone, cyclohexyladipates are formed and removed from the lower portion of the reaction zone and benzene is removed from the upper portion of the reaction zone. The reaction zone also contains an acid catalyst.

U.S. Pat. No. 5,321,157 (Kollar) discloses a process for the preparation of $C_5$–$C_8$ aliphatic dibasic acids through oxidation of corresponding saturated cycloaliphatic hydrocarbons by
 (1) reacting, at a cycloaliphatic hydrocarbon conversion level of between about 7% and about 30%,
  (a) at least one saturated cycloaliphatic hydrocarbon having from 5 to 8 ring carbon atoms in the liquid phase and
  (b) an excess of oxygen gas or an oxygen containing gas mixture
 in the presence of
  (c) less than 1.5 moles of a solvent per mole of cycloaliphatic hydrocarbon (a), wherein said solvent comprises an organic acid containing only primary and/or secondary hydrogen atoms and
  (d) at least about 0.002 mole per 1000 grams of reaction mixture of a polyvalent heavy metal catalyst; and
 (2) isolating the $C_5$–$C_8$ aliphatic dibasic acid.

U.S. Pat. No. 5,221,800 (Park et al.) discloses a process for the manufacture of adipic acid is disclosed. In this process, cyclohexane is oxidized in an aliphatic monobasic acid solvent in the presence of a soluble cobalt salt wherein water is continuously or intermittently added to the reaction system after the initiation of oxidation of cyclohexane as indicated by a suitable means of detection, and wherein the reaction is conducted at a temperature of about 50° C. to about 150° C. at an oxygen partial pressure of about 50 to 420 pounds per square inch absolute.

U.S. Pat. No. 3,987,100 (Barnette et al.) describes a process of oxidizing cyclohexane to produce cyclohexanone and cyclohexanol, said process comprising contacting a stream of liquid cyclohexane with oxygen in each of at least three successive oxidation stages by introducing into each stage a mixture of gases comprising molecular oxygen and an inert gas.

U.S. Pat. No. 3,957,876 (Rapoport et al.) describes a process for the preparation of cyclohexyl hydroperoxide substantially free of other peroxides by oxidation of cyclohexane containing a cyclohexane soluble cobalt salt in a zoned oxidation process in which an oxygen containing gas is fed to each zone in the oxidation section in an amount in excess of that which will react under the conditions of that zone.

U.S. Pat. No. 3,932,513 (Russell) discloses the oxidation of cyclohexane with molecular oxygen in a series of reaction zones, with vaporization of cyclohexane from the last reactor effluent and parallel distribution of this cyclohexane vapor among the series of reaction zones.

U.S. Pat. No. 3,530,185 (Pugi) discloses a process for manufacturing precursors of adipic acid by oxidation with an oxygen-containing inert gas which process is conducted in at least three successive oxidation stages by passing a stream of liquid cyclohexane maintained at a temperature in the range of 140° C. to 200° C. and a pressure in the range of 50 to 350 p.s.i.g. through each successive oxidation stage and by introducing a mixture of gases containing oxygen in each oxidation stage in an amount such that substantially all of the oxygen introduced into each stage is consumed in that stage thereafter causing the residual inert gases to pass countercurrent into the stream of liquid during the passage of the stream through said stages.

U.S. Pat. No. 3,515,751 (Oberster et al.) discloses a process for the production of epsilon-hydroxycaproic acid in which cyclohexane is oxidized by liquid phase air oxidation in the presence of a catalytic amount of a lower aliphatic carboxylic acid and a catalytic amount of a peroxide under certain reaction conditions so that most of the oxidation products are found in a second, heavy liquid layer, and are directed to the production of epsilon-hydroxycaproic acid.

U.S. Pat. No. 3,361,806 (Lidov et al.) discloses a process for the production of adipic acid by the further oxidation of the products of oxidation of cyclohexane after separation of cyclohexane from the oxidation mixture, and more particularly to stage wise oxidation of the cyclohexane to give high yields of adipic acid precursors and also to provide a low enough concentration of oxygen in the vent gas so that the latter is not a combustible mixture.

U.S. Pat. No. 3,234,271 (Barker et al.) discloses a process for the production of adipic acid by the two-step oxidation of cyclohexane with oxygen. In a preferred embodiment, mixtures comprising cyclohexanone and cyclohexanol are oxidized. In another embodiment, the process involves the production of adipic acid from cyclohexane by oxidation thereof, separation of cyclohexane from the oxidation mixture and recycle thereof, and further oxidation of the other products of oxidation.

U.S. Pat. No. 3,231,608 (Kollar) discloses a process for the preparation of aliphatic dibasic acids from saturated cyclic hydrocarbons having from 4 to 8 cyclic carbon atoms per molecule in the presence of a solvent which comprises an aliphatic monobasic acid which contains only primary and secondary hydrogen atoms and a catalyst comprising a cobalt salt of an organic acid, and in which process the molar ratio of said solvent to said saturated cyclic hydrocarbon is between 1.5:1 and 7:1, and in which process the molar ratio of said catalyst to said saturated cyclic hydrocarbon is at least 5 millimoles per mole.

U.S. Pat. No. 3,161,603 (Leyshon et al.) discloses a process for recovering the copper-vanadium catalyst from the waste liquors obtained in the manufacture of adipic acid by the nitric acid oxidation of cyclohexanol and/or cyclohexanone.

U.S. Pat. No. 2,565,087 (Porter et al.) discloses the oxidation of cycloaliphatic hydrocarbons in the liquid phase with a gas containing molecular oxygen and in the presence of about 10% water to produce two phases and avoid formation of esters.

U.S. Pat. No. 2,557,282 (Hamblet et al.) discloses production of adipic acid and related aliphatic dibasic acids; more particularly to the production of adipic acid by the direct oxidation of cyclohexane.

U.S. Pat. No. 2,439,513 (Hamblet et al.) discloses the production of adipic acid and related aliphatic dibasic acids and more particularly to the production of adipic acid by the oxidation of cyclohexane.

U.S. Pat. No. 2,223,494 (Loder et al.) discloses the oxidation of cyclic saturated hydrocarbons and more particularly to the production of cyclic alcohols and cyclic ketones by oxidation of cyclic saturated hydrocarbons with an oxygen-containing gas.

U.S. Pat. No. 2,223,493 (Loder et al.) discloses the production of aliphatic dibasic acids and more particularly to the production of aliphatic dibasic acids by oxidation of cyclic saturated hydrocarbons with an oxygen-containing gas.

German Pat. No. DE 44 26 132 A 1 (Kysela et al.) discloses a method for dehydration of process acetic acid from the liquid-phase oxidation of cyclohexane with air, in the presence of cobalt salt as a catalyst after separation of the adipic acid by filtration and the cyclohexane phase by phase separation, while simultaneously avoiding cobalt salt precipitates in the dehydration column, characterized in that the acetic acid phase to be returned to the beginning of the process is subjected to azeotropic distillation by the use of added cyclohexane, under distillative removal of the water down to a residual content of less than about 0.3 to 0.7 wt %.

PCT Demand International publication WO 96/03365 (Costantini et al.) discloses a method of recycling a cobalt-containing catalyst in a reaction involving the direct oxidation of cyclohexane into adipic acid using an oxygen containing gas. The method is characterized in that the reaction mixture, obtained in a preceding stage where the cyclohexane was oxidized into adipic acid, of which at least part of the intermediate oxidation products, such as cyclohexanol and cyclohexanone, the carboxylic acid and water has been separated and of which at least part of the adipic acid formed has been recovered by crystallization, undergoes at least one extraction operation using at least one co-solvent or a mixture comprising a co-solvent and a carboxylic acid. The method is also characterized by the separation of a mixture containing at least part of the cobalt catalyst, part of the carboxylic acid and optionally residual quantities of other compounds and a solution containing the co-solvent and at least part of the glutaric and succinic acids formed during the oxidation reaction, and the carboxylic acid.

None of the above references, or any other references known to the inventors disclose, suggest or imply, singly or in combination, oxidation of hydrocarbons to intermediate oxidation products, such as monobasic acids, dibasic acids, etc., in the presence of an activated initiator, subject to the intricate and critical controls and requirements of the instant invention as described and claimed.

Our U.S. Pat. Nos. 5,580,531, 5,558,842, 5,502,245, and our co-pending applications 08/477,195 (filed Jun. 7, 1995), 08/587,967 (filed Jan. 17, 1996), and 08/620,974 (filed Mar. 25, 1996), now U.S. Pat. No. 5,654,475, all of which are incorporated herein by reference, describe methods and apparatuses relative to controlling reactions in atomized liquids.

Our co-pending application, Docket No. T-603, of Mark W. Dassel, Eustathios Vassiliou, David C. DeCoster, Ader M. Rostami, and Sharon M. Aldrich, titled "Methods and Devices for Controlling the Reaction Rate of a Hydrocarbon to an Acid by Making Phase-related Adjustments," filed on Mar. 6, 1997, and having a Ser. No. 08/812,847, is also incorporated herein by reference.

Our co-pending application, Docket No. T-701, of Mark W. Dassel, David C. DeCoster, Ader M. Rostami, Sharon M. Aldrich, and Eustathios Vassiliou, titled "Methods and Devices for Preparing Dibasic Acids," filed on Mar. 27, 1997, and having a Ser. No. 08/824,992, is also incorporated herein by reference.

All of the following patent applications, which were filed simultaneously with the present application are also incorporated herein by reference:

Docket No. U.S. patent application Ser. No. 08/859,985 of Eustathios Vassiliou, Mark W. Dassel, David C. DeCoster, Ader M. Rostami, and Sharon M. Aldrich, titled "Methods and Devices for Controlling the Reaction Rate of a Hydrocarbon to an Intermediate Oxidation Product by Pressure Drop Adjustments";

Docket No. U.S. patent application Ser. No. 08/861,281 of Mark W. Dassel, Eustathios Vassiliou, David C. DeCoster, Ader M. Rostami, and Sharon M. Aldrich, titled "Methods and Devices for Controlling the Reaction Rate of a Hydrocarbon to an Intermediate Oxidation Product by Monitoring Flow of Incoming and Outcoming Gases";

Docket No. U.S. patent application Ser. No. 08/861,180 of David C. DeCoster, Ader M. Rostami, Mark W. Dassel, and Eustathios Vassiliou, titled "Methods and Devices for Controlling the Oxidation Rate of a Hydrocarbon by Adjusting the Ratio of the Hydrocarbon to a Rate-Modulator";

Docket No. U.S. patent application Ser. No. 08/859,890 of Ader M. Rostami, Mark W. Dassel, Eustathios Vassiliou, David C. DeCoster, titled "Methods and Devices for Controlling the Oxidation of a Hydrocarbon to an Acid by Regulating Temperature/Conversion Relationship in Multi-Stage Arrangements"; and Docket No. U.S. patent application Ser. No. 08/861,210 of Eustathios Vassiliou, Ader M. Rostami, David C. DeCoster, and Mark W. Dassel, titled "Pseudo-Plug-Flow Reactor."

SUMMARY OF THE INVENTION

As aforementioned, this invention relates to methods of making intermediate oxidation products by oxidizing a hydrocarbon with a gas containing an oxidant, preferably oxygen. More particularly, it relates to a method of preparing an intermediate oxidation product from a hydrocarbon comprising the steps of:

(a) feeding a hydrocarbon and an initiator into a first reaction zone at a first hydrocarbon to initiator ratio by weight;

(b) oxidizing partially at least one of said hydrocarbon and initiator to form a first mixture;

(c) mixing the first mixture with a second mixture comprising the same hydrocarbon and initiator, the hydrocarbon and the initiator of the second mixture being present at a second hydrocarbon to initiator ratio by weight higher than the first hydrocarbon to initiator ratio;

(d) further oxidizing said hydrocarbon to a desired degree.

At least one of steps (c) and (d) may be conducted in a second reaction zone different than the first reaction zone, or at least one of steps (b), (c), and (d) may be conducted in the first reaction zone. Thus, in this method, just one reaction zone may be used or more than one reaction zones.

Preferably, the method comprises a step of introducing into at least one of the first and the second reaction zone at least one ingredient selected from a group consisting of solvent and catalyst. The solvent preferably comprises an acid, and more preferably acetic acid. The catalyst preferably comprises a cobalt compound, and more preferably cobalt acetate.

Preferably, the first hydrocarbon to initiator ratio is in the range of 0/1 to 50/1, and the second hydrocarbon to initiator ratio is in the range of 10/1 to 1000/1, provided as aforementioned that the first hydrocarbon to initiator ratio is lower than the second hydrocarbon to initiator ratio.

The initiator may preferably be a ketone, the ketone corresponding to an oxidation product of the hydrocarbon, or it may be an aldehyde, the aldehyde being a reduction product of the acid. For example if the hydrocarbon is cyclohexane, it is preferable that the initiator is cyclohexanone. Similarly, if the acid is acetic acid the initiator may be acetaldehyde. If the hydrocarbon is cyclohexane and the acid is acetic acid, the initiator may preferably be either cyclohexanone or acetaldehyde or a combination thereof. However, it is preferable that it is cyclohexanone.

The processes of the instant invention are particularly suited in the case that the hydrocarbon comprises cyclohexane, the intermediate oxidation product comprises adipic acid, the initiator comprises cyclohexanone, the solvent comprises acetic acid, and the catalyst comprises a cobalt compound.

Preferably, the first mixture and the second mixture are mixed at a first mixture to second mixture ratio (third ratio) in the range of 1/5 to 1/500, more preferably in the range of 1/10 to 1/200, and even more preferably in the range of 1/20 to 1/100. Preferably, the conversion of hydrocarbon and initiator to all oxidation products, in the first zone, is maintained in the range of 5–90%, more preferably in the range of 10–80%, and even more preferably in the range of 20–60%.

This arrangement of the instant invention, may substantially eliminate the initiation delay, while providing good selectivity and yield.

In a different example, the hydrocarbon may be an aromatic compound having methyl groups. The aromatic compound preferably comprises a moiety selected from a group consisting of toluene, o-xylene, p-xylene, m-xylene and a mixture thereof, and the intermediate oxidation product comprises a moiety selected from a group consisting of benzoic acid, phthalic acid, isophthalic acid, terephthalic acid, and a mixture thereof.

Further, the instant invention pertains to a method, wherein the intermediate oxidation product comprises a compound selected from a group consisting of adipic acid, phthalic acid, isophthalic acid, and terephthalic acid, and the method further comprises a step of reacting said intermediate oxidation product with a third reactant selected from a group consisting of a polyol, a polyamine, and a polyamide in a manner to form a polymer of a polyester, or a polyamide, or a (polyimide and/or polyamideimide), respectively.

The method may further comprise a step of spinning the polymer into fibers.

BRIEF DESCRIPTION OF THE DRAWING

The reader's understanding of this invention will be enhanced by reference to the following detailed description taken in combination with the drawing figures, wherein.

DETAILED DESCRIPTION OF THE INVENTION

Figure 1:
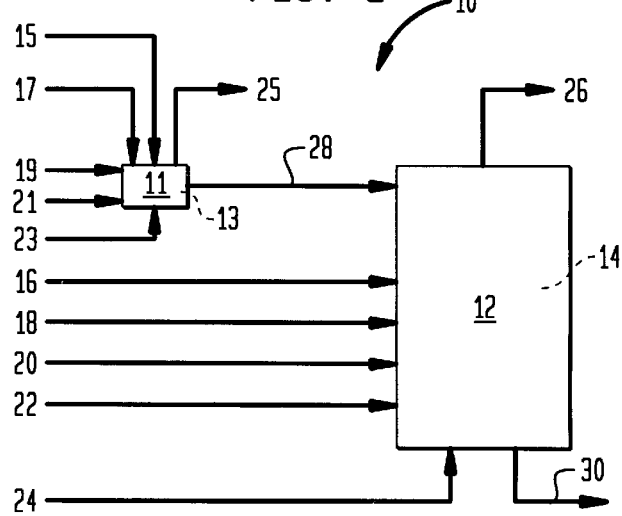
FIG. 1 illustrates schematically an apparatus in relevance to a preferred embodiment of the present invention.

As mentioned earlier, this invention relates to methods of making intermediate oxidation products, such as acids, for example, by oxidizing a hydrocarbon with a gas containing an oxidant, preferably oxygen.

The methods of the present invention may be applied preferably to acids from the corresponding hydrocarbons. Examples are formation of adipic acid from cyclohexane, of glutaric acid from cyclopentane, of pimelic acid from cycloheptane, of benzoic acid from toluene, of phthalic acid from o-xylene, of isophthalic acid from mxylene, of terephthalic acid from p-xylene, and the like. It should be pointed out, however, that this invention is not limited to formation of acids, but to intermediate oxidation products different than oxides of carbon. Examples of other intermediate oxidation products are cyclohexanone, cyclohexanol, cyclohexylhydroperoxide, mixtures thereof, and the like.

As aforementioned, initiators have been used so far to initiate a reaction, such as oxidation of cyclohexane to adipic acid, for example. This initiation of reaction or oxidation shortens an induction period considerably. The induction period in their absence is in most occasions unacceptably long, frequently of the order of days, while in their presence, the induction period is rather short, frequently of the order of a fraction of one hour. The explanation accepted by many researchers is that the initiators induce oxidation of the catalyst, which usually comprises cobaltous ions, to cobaltic ions. Cobaltic ions are important in the mechanism of oxidations, such as the oxidation of cyclohexane to adipic acid for example. After a certain amount of cobaltic ions have been formed, the mechanisms proposed involve a combination of cobaltous and cobaltic ions, both of which are considered as being regenerated through formation of intermediate species during the oxidation. Examples of initiators include but are not limited to acetaldehyde, cyclohexanone, methylethylketone, etc.

According to this invention, the oxidation is initiated in an abundance of initiator, and then it is continued in the presence of a rather small amount of initiator, adequate to allow the oxidation to proceed at a reasonable rate. When the initiator is in great abundance, the reaction is fast, and if the amount of initiator is high enough the initiation period is eliminated for all practical purposes, so that the reaction proceeds immediately. Under conditions, the selectivity and yield of intermediate oxidation product from the hydrocarbon and/or initiator, may suffer in the first reaction zone. However, by mixing a rather small amount of the first mixture with a considerably larger amount of the second mixture, the overall selectivity and yield (after the hydrocarbon has been oxidized to the desired degree in the second reaction zone) become insignificant. Preferably, the first mixture and the second mixture are mixed at a first mixture to second mixture ratio in the range of 1/5 to 1/500, more preferably in the range of 1/10 to 1/200, and even more preferably in the range of 1/20 to 1/100. Preferably, the conversion of hydrocarbon and initiator to all oxidation products, in the first zone, is maintained in the range of 5–90%, more preferably in the range of 10–80%, and even more preferably in the range of 20–60%.

This arrangement of the instant invention, may substantially eliminate the initiation delay, while providing good selectivity and yield. The two steps discussed above may take place in one or in more than one reaction zones.

In most oxidations, according to the present invention, a solvent is involved, such as acetic acid for example. If an aldehyde is used as an initiator, it is preferable that the aldehyde corresponds to the acid used as solvent in the oxidation reaction. If acetic acid is the solvent used in the oxidation, for example, acetaldehyde should preferably be used as an initiator. Similarly, if an aldehyde is to be used in an oxidation as an initiator, and if the solvent is propionic acid, propionaldehyde should be preferably utilized. The use of acetic acid as solvent is highly preferred, because it is considerably more stable than other organic acids. Use of the corresponding aldehyde is preferable because if oxidized it turns to the corresponding acid. Thus, if acetaldehyde is used as an initiator, and if it is oxidized it turns to acetic acid which is the solvent.

In a similar manner, if a ketone is used as the initiator, it is preferable that the ketone corresponds to the hydrocarbon which is to be oxidized. Thus, for example, in the case that the hydrocarbon to be oxidized to adipic acid is cyclohexane, the preferable ketone to be used as an initiator should be cyclohexanone. Use of cyclohexanone as an initiator, in the case of direct synthesis of adipic acid, is of particular interest because cyclohexane may initially be partially oxidized to form just a small appropriate amount of cyclohexanone, and then further oxidized to adipic acid.

In FIG. 1, there is depicted a reactor system 10, which may be used for practicing a preferred embodiment of the instant invention. The reactor system 10 comprises an initiator activation chamber 11, which in turn comprises a first reaction zone 13. Feeding lines 15, 17, 19, 21 and 23 are connected to the initiator activation chamber 11 for feeding initiator, hydrocarbon, catalyst, solvent, and oxidant, respectively, to the first reaction zone 13. Of course, premixing of two or more of the above ingredients may take place at an earlier stage, and the resulting mixture may be fed to the reaction zone 13 as one stream. An outlet gas line 25 may be used to remove off-gases.

The reactor system 10 also comprises a reaction chamber 12, which in turn comprises a second reaction zone 14. Feeding lines 16, 18, 20, 22 and 24 are connected to the reaction chamber 12 for feeding initiator, hydrocarbon, catalyst, solvent, and oxidant, respectively, to the second reaction zone 14. Of course, premixing of two or more of the above ingredients may take place at an earlier stage, and the resulting mixture may be fed to the reaction zone 14 as one stream. An outlet gas line 26 may be used to remove off-gases. Transfer line 28 connects the initiator activation chamber 11 with the reaction chamber 12, and it is used for transferring activated initiator from the initiator activation chamber 11 to the reaction chamber 12. A liquid exit line 30 is also connected to the reaction chamber 12 for removing oxidized substantially liquid products from the reaction zone 14.

Miscellaneous accessories, such as for example, temperature measuring and control devices, pressure measuring and control devices, heaters, coolers, heat exchangers, reflux devices, valves, pumps, controllers, feed-back and control lines, oxidation-product treatment devices, and others, are not shown in FIG. 1 for purposes of clarity and brevity. Examples of such accessories are given in our aforementioned patents and patent applications.

The initiator activation chamber 11 and/or the reaction chamber 12 may be of the atomization type, the stirred-tank reactor type, the plug-flow reactor type, or any other suitable type, depending on the individual circumstances.

In operation of this embodiment, initiator is fed to the activation chamber 11 through feed line 15, and hydrocarbon through feed line 17. The operation of the preferred embodiments of this invention may be better understood if it is presented in the form of examples. For example, in the case that the hydrocarbon is cyclohexane and the intermediate oxidation product is adipic acid, the initiator, which is preferably cyclohexanone or acetaldehyde, and more preferably cyclohexanone is introduced through feed line 15, while the hydrocarbon, being in this example cyclohexane is introduced through feed line 17. It is preferable that a first ratio of the flows of cyclohexane to cyclohexanone fed to the activation chamber 11 is lower than 50 to 1. More preferably, especially in the case that cyclohexanone is used as initiator, no hydrocarbon is fed into the initiator activation chamber 11, thus the first ratio being 0 to 1. In the case of other initiators, such as acetaldehyde for example, it is preferable that at least some hydrocarbon, cyclohexane for example is also fed to the activation chamber 11. It is also preferable that a catalyst, for example cobalt acetate, and a solvent, for example acetic acid, enter the initiator activation chamber 11 through feed lines 19 and 21, respectively. The feed rate of catalyst is preferably 1 to 20% based on the sum of feeds of catalyst plus initiator plus hydrocarbon plus solvent, by weight, and more preferably 2 to 10%. The rate of solvent fed should preferably be 50 to 90% of the total feed to the initiator activation chamber. The catalyst is preferably fed dissolved in the solvent.

Oxidant, which is preferably a gaseous mixture of an inert gas, such as nitrogen for example mixed with oxygen, or just oxygen, enters the initiator activation chamber 11 through feed line 23. Off gases may leave the system through outlet line 25. The reaction starts very fast, if not immediately, due to the large amount of initiator present, thus substantially eliminating any induction period. In the case of adipic acid as the intermediate oxidation product, the temperature is preferably maintained in the range of 70° C. to 120° C., and more preferably in the range of 90° C. to 110° C. The partial pressure of oxygen is preferably maintained in the range of 50 to 500 p.s.i. and more preferably in the range of 100 to 200 p.s.i.

In sequence, liquid containing partially converted hydrocarbon and/or initiator is being transferred to the reaction chamber 12 through transfer line 28 at a desired flow rate, and it is mixed in the second reaction zone 14 with additional hydrocarbon entering the second reaction zone 14 through feed line 18. Additional initiator, catalyst and solvent may enter the reaction zone 14 of the reaction chamber 12 through feed lines 16, 20, and 22, respectively, if so desired. It is critical that the first ratio of hydrocarbon to initiator entering the reaction zone 11 through lines 17 and 15, respectively, is lower than second ratio of hydrocarbon to initiator entering the reaction zone 14 through feed lines 18 and 16, respectively. All the ingredients being fed to the reaction zone 14 are eventually mixed, and the hydrocarbon is oxidized by oxidant (preferably oxygen or a mixture of oxygen and inert gas) entering the reaction zone 14 through feed line 24. The oxidized (to a desired degree) hydrocarbon leaves the reaction zone 14 of the reaction chamber 12 through liquid exit line 30 for separation of the intermediate product (adipic acid in this example), and further treatment for removal of by-products, recycling unreacted matter, and the like. Continual or periodic analysis of the contents of the two reaction zones assists in achieving good control of the process.

Pressures and temperatures in the second reaction zone may be the same or different than the ones prevailing in the first reaction zone.

It is highly preferable, at least in the case that the hydrocarbon is cyclohexane, the initiator is cyclohexanone, and the intermediate oxidation product is adipic acid, to feed no hydrocarbon in the first reaction zone 13, and to feed no additional initiator in the second reaction zone 14.

The operations performed in the activation chamber 11 and the reaction chamber 12, may be conducted in the reaction chamber 12, in the case of a batch system for example. According to this embodiment, the activation chamber 11 and the transfer line 28 are omitted. Initially, initiator and hydrocarbon are added to the chamber, preferably in an abundance of initiator, and an oxidation is initiated to a desired low degree of conversion. Catalyst and initiator are preferably also added. When this task is performed, a mixture is produced in the reaction zone 14, having an excess of hydrocarbon as compared to the initial mixture, by feeding desired amounts of initiator, hydrocarbon, catalyst and solvent through feed lines 16, 18, 20, and 22, respectively. The oxidation of the hydrocarbon is continued to a desired degree, and the contents of the reaction chamber 12 are released through line 30 for further treatment, recycling, etc.

Figure 2:
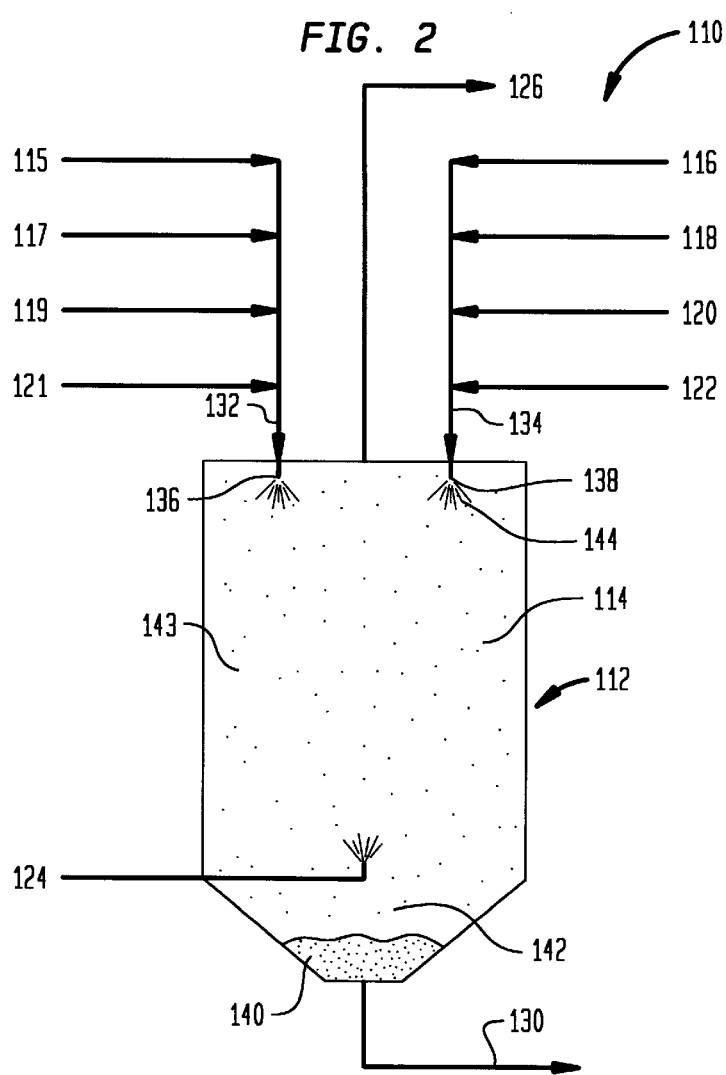
FIG. 2 illustrates schematically a different apparatus in relevance to another preferred embodiment of the present invention, wherein atomization is employed.

In still another embodiment of the instant invention, better illustrated in FIG. 2, there is provided an atomization reaction chamber 112, which includes a first reaction zone 114. There are also provided feed lines 115, 117, 119, and 121, for feeding initiator, hydrocarbon, catalyst, and solvent, respectively. These lines merge to a first mixture feed line 132, which in turn leads to a first sprayer or atomizer. Similarly, there are further provided feed lines 116, 118, 120, and 122 for feeding initiator, hydrocarbon, catalyst, and solvent, respectively. These lines merge to a second mixture feed line 134, which in turn leads to a second sprayer 138.

Intermediate vessels, heaters, other elements mentioned hereinabove, etc. which may be used as linkages from individual feed lines to the mixture feed lines are not shown for purposes of clarity and brevity.

A gaseous oxidant feed line 124 and outlet gas line 126 are also provided, serving the same purposes as lines 24 and 26, respectively.

In operation of this embodiment, a first mixture having similar composition as the first mixture passing through transfer line 28 of FIG. 1, is provided to the first sprayer 136 (FIG. 2) through the first mixture line 132. The first mixture is atomized at the sprayer into first droplets 143, which remain suspended in the reaction zone 114 for a first period of time before they coalesce into a liquid 140 at the lower portion 142 of the reaction chamber 112. This first period of time depends and can be controlled by the first droplet size, upward gaseous movement, and other parameters. At the same time, the second mixture, passing through line 134, is also atomized by the second sprayer 138 into second droplets 144. This second mixture is similar in composition to the second mixture produced by the feed lines 16, 18, 20, and 22, as explained in the first embodiment described above in relevance to FIG. 1. The second droplets also remain suspended in the reaction zone 114 for a second period of time before they coalesce into the liquid 140 at the lower portion 142 of the reaction chamber 112. This second period of time depends and can be controlled by the second droplet size, upward gaseous movement, and other parameters in a similar manner as the first droplets. Due to the inherent individuality of the droplets, the majority of the first and the second droplets do not mix before they coalesce into the liquid 140. The liquid 140, comprising the coalesced first and second droplets is partially transferred to appropriate equipment (not shown) for further treatment, and partially is transferred (not shown) to the second mixture line 134 for recycling. As the first droplets 143 travel from the first atomizer 136 to the liquid 140, they start being oxidized much faster than the second droplets 144, since they contain a higher percentage of initiator than said second droplets 144. In this manner both the first and the second mixture are being oxidized in the same reaction zone.

It is preferable that no hydrocarbon is fed to the atomizer 136 through the first mixture line 132, and also it is preferable that no additional initiator is fed to the second atomizer 138 through the second mixture line 134.

In this arrangement, it is also preferable that any new initiator needed to replenish any oxidized or otherwise lost initiator after recycling, is added through line 115, while any new hydrocarbon needed to replenish any oxidized or otherwise lost hydrocarbon after recycling, is added through line 118. Similarly, any additional catalyst and additional solvent should preferably be added through lines 119 and 121, respectively. Liquid 140, leaving the reaction zone through line 130 may preferably be partially fed directly to the reaction zone 114 through line 134 and partially fed to the same zone through line 134 after further treatment.

In the different figures of the drawing, numerals differing by 100 represent elements which are either substantially the same or perform the same function. Therefore, in the case that one element has been defined once in a certain embodiment, its re-definition in other embodiments illustrated in the figures by the same numerals or numerals differing by 100 is not necessary, and it has been often omitted in the above description for purposes of brevity.

Oxidations according to this invention, are non-destructive oxidations, wherein the intermediate oxidation product is defined as being a compound different than carbon monoxide, carbon dioxide, and a mixture thereof. Of course, small amounts of these compounds may be formed along with the intermediate oxidation product, which may be one product or a mixture of products.

Examples include, but of course, are not limited to preparation of aliphatic dibasic acids from the corresponding saturated cycloaliphatic hydrocarbons, such as for example preparation of adipic acid from cyclohexane.

Regarding adipic acid, the preparation of which is especially suited to the methods and apparatuses of this invention, general information may be found in a plethora of U.S. Patents, among other references. These, include, but are not limited to:

U.S. Pat. Nos. 2,223,493; 2,589,648; 2,285,914; 3,231,608; 3,234,271; 3,361,806; 3,390,174; 3,530,185; 3,649,685; 3,657,334; 3,957,876; 3,987,100; 4,032,569; 4,105,856; 4,158,739 (glutaric acid); 4,263,453; 4,331,608; 4,606,863; 4,902,827; 5,221,800; and 5,321,157.

Diacids (for example adipic acid, phthalic acid, isophthalic acid, terephthalic acid, and the like) or other suitable compounds may be reacted, according to well known to the art techniques, with a third reactant selected from a group consisting of a polyol, a polyamine, and a polyamide in a manner to form a polymer of a polyester, or a polyamide, or a (polyamide and/or polyamideimide), respectively. Preferably the polyol, the polyamine, and the polyamide are mainly a diol, a diamine, and a diamide, respectively, in order to avoid excessive cross-linking. The polymer resulting from this reaction may be spun by well known to the art techniques to form fibers.

Examples demonstrating the operation of the instant invention have been given for illustration purposes only, and should not be construed as limiting the scope of this invention in any way. In addition it should be stressed that the preferred embodiments discussed in detail hereinabove, as well as any other embodiments encompassed within the limits of the instant invention, may be practiced individually, or in any combination thereof, according to common sense and/or expert opinion. Individual sections of the embodiments may also be practiced individually or in combination with other individual sections of embodiments or embodiments in their totality, according to the present invention. These combinations also lie within the realm of the present invention. Furthermore, any attempted explanations in the discussion are only speculative and are not intended to narrow the limits of this invention.

All explanations given hereinabove are to be considered as speculative and should not be construed as limiting the breadth of the claims.

All ratios are by weight.

What is claimed is:

1. A method of preparing an intermediate oxidation product from a hydrocarbon comprising the steps of:
    (a) feeding a hydrocarbon and an initiator into a first reaction zone at a first hydrocarbon to initiator ratio by weight;
    (b) oxidizing partially at least one of said hydrocarbon and initiator to form a first mixture;
    (c) mixing the first mixture with a second mixture comprising the same hydrocarbon and initiator, the hydrocarbon and the initiator of the second mixture being present at a second hydrocarbon to initiator ratio by weight higher than the first hydrocarbon to initiator ratio, wherein the first mixture and the second mixture are mixed at a third ratio of first mixture to second mixture lower than 1; and
    (d) further oxidizing said hydrocarbon to a desired degree.

2. A method of preparing an intermediate oxidation product from a hydrocarbon comprising the steps of:
    (a) feeding a hydrocarbon and an initiator into a first reaction zone at a first hydrocarbon to initiator ratio by weight;
    (b) oxidizing partially at least one of said hydrocarbon and initiator to form a first mixture;
    (c) mixing the first mixture with a second mixture comprising the same hydrocarbon and initiator, the hydrocarbon and the initiator of the second mixture being present at a second hydrocarbon to initiator ratio by weight higher than the first hydrocarbon to initiator ratio, wherein the first mixture and the second mixture are mixed at a third ratio of first mixture to second mixture lower than 1; and
    (d) further oxidizing said hydrocarbon to a desired degree, wherein steps (c) and (d) are conducted in a second reaction zone different than the first reaction zone.

3. A method as defined in claim 1, wherein steps (a), (b), (c), and (d) are conducted in the first reaction zone.

4. A method as defined in claim 2, further comprising a step of introducing into at least one of the first and the second reaction zone at least one ingredient selected from a group consisting of solvent and catalyst.

5. A method as defined in claim 3, further comprising a step of introducing into the first reaction zone at least one ingredient selected of a group consisting of solvent and catalyst.

6. A method as defined in claim 1, further comprising a step of introducing into the first reaction zone at least one ingredient selected of a group consisting of solvent and catalyst.

7. A method as defined in claim 1, wherein the first hydrocarbon to initiator ratio is in the range of 0/1 to 50/1.

8. A method as defined in claim 1, wherein the second hydrocarbon to initiator ratio is in the range of 10/1 to 1000/1.

9. A method as defined in claim 7, wherein the second hydrocarbon to initiator ratio is in the range of 10/1 to 1000/1.

10. A method as defined in claim 1, wherein the initiator is a ketone, the ketone corresponding to an oxidation product of the hydrocarbon.

11. A method as defined in claim 4, wherein the solvent is an acid and the initiator is a compound selected from a group consisting of a ketone, the ketone corresponding to an oxidation product of the hydrocarbon and an aldehyde, the aldehyde being a reduction product of the acid.

12. A method as defined in claim 5, wherein the solvent is an acid and the initiator is a compound selected from a group consisting of a ketone, the ketone corresponding to an oxidation product of the hydrocarbon and an aldehyde, the aldehyde being a reduction product of the acid.

13. A method as defined in claim 6, wherein the solvent is an acid and the initiator is a compound selected from a group consisting of a ketone, the ketone corresponding to an oxidation product of the hydrocarbon and an aldehyde, the aldehyde being a reduction product of the acid.

14. A method of preparing an intermediate oxidation product from a hydrocarbon comprising the steps of:
(a) feeding a hydrocarbon and an initiator into a first reaction zone at a first hydrocarbon to initiator ratio by weight;
(b) oxidizing partially at least one of said hydrocarbon and initiator to form a first mixture;
(c) mixing the first mixture with a second mixture comprising the same hydrocarbon and initiator, the hydrocarbon and the initiator of the second mixture being present at a second hydrocarbon to initiator ratio by weight higher than the first hydrocarbon to initiator ratio, wherein the first mixture and the second mixture are mixed at a third ratio of first mixture to second mixture lower than 1; and
(d) further oxidizing said hydrocarbon to a desired degree; wherein the hydrocarbon comprises cyclohexane and the intermediate oxidation product comprises adipic acid.

15. A method as defined in claim 2, wherein the hydrocarbon comprises cyclohexane and the intermediate oxidation product comprises adipic acid.

16. A method as defined in claim 3, wherein the hydrocarbon comprises cyclohexane and the intermediate oxidation product comprises adipic acid.

17. A method as defined in claim 4, wherein the hydrocarbon comprises cyclohexane, the intermediate oxidation product comprises adipic acid, the initiator comprises cyclohexanone, the solvent comprises acetic acid, and the catalyst comprises a cobalt compound.

18. A method as defined in claim 5, wherein the hydrocarbon comprises cyclohexane, the intermediate oxidation product comprises adipic acid, the initiator comprises cyclohexanone, the solvent comprises acetic acid, and the catalyst comprises a cobalt compound.

19. A method as defined in claim 6, wherein the hydrocarbon comprises cyclohexane, the intermediate oxidation product comprises adipic acid, the initiator comprises cyclohexanone, the solvent comprises acetic acid, and the catalyst comprises a cobalt compound.

20. A method as defined in claim 7, wherein the hydrocarbon comprises cyclohexane, the intermediate oxidation product comprises adipic acid, the initiator comprises cyclohexanone, the solvent comprises acetic acid, and the catalyst comprises a cobalt compound.

21. A method as defined in claim 8, wherein the hydrocarbon comprises cyclohexane, the intermediate oxidation product comprises adipic acid, the initiator comprises cyclohexanone, the solvent comprises acetic acid, and the catalyst comprises a cobalt compound.

22. A method as defined in claim 9, wherein the hydrocarbon comprises cyclohexane, the intermediate oxidation product comprises adipic acid, the initiator comprises cyclohexanone, the solvent comprises acetic acid, and the catalyst comprises a cobalt compound.

23. A method as defined in claim 11, wherein the acid is acetic acid and the initiator is acetaldehyde.

24. A method as defined in claim 12, wherein the acid is acetic acid and the initiator is acetaldehyde.

25. A method as defined in claim 13, wherein the acid is acetic acid and the initiator is acetaldehyde.

26. A method as defined in claim 1, wherein the hydrocarbon is an aromatic compound containing methyl groups.

27. A method as defined in claim 1, wherein the hydrocarbon comprises a moiety selected from a group consisting of toluene, o-xylene, p-xylene, m-xylene and a mixture thereof, and the intermediate oxidation product comprises a moiety selected from a group consisting of benzoic acid, phthalic acid, isophthalic acid, terephthalic acid, and a mixture thereof.

28. A method as defined in claim 2, wherein the hydrocarbon comprises a moiety selected from a group consisting of toluene, o-xylene, p-xylene, m-xylene and a mixture thereof, and the intermediate oxidation product comprises a moiety selected from a group consisting of benzoic acid, phthalic acid, isophthalic acid, terephthalic acid, and a mixture thereof.

29. A method as defined in claim 3, wherein the hydrocarbon comprises a moiety selected from a group consisting of toluene, o-xylene, p-xylene, m-xylene and a mixture thereof, and the intermediate oxidation product comprises a moiety selected from a group consisting of benzoic acid, phthalic acid, isophthalic acid, terephthalic acid, and a mixture thereof.

30. A method as defined in claim 1, wherein a catalyst is added in at least step (a).

31. A method as defined in claim 2, further comprising a step of introducing a catalyst into at least the first reaction zone.

32. A method as defined in claim 3, further comprising a step of introducing a catalyst into the first reaction zone.

33. A method as defined in claim 30, wherein a solvent is added in at least step (c).

34. A method as defined in claim 31, further comprising a step of introducing a solvent into at least the first reaction zone.

35. A method as defined in claim 32, further comprising a step of introducing a solvent into the first reaction zone.

36. A method as defined in claim 1, wherein the first mixture and the second mixture are mixed at a third ratio of first mixture to second mixture lower than 1.

37. A method as defined in claim 36, wherein the third ratio is in the range of 1/5 to 1/500.

38. A method as defined in claim 37, wherein the third ratio is in the range of 1/10 to 1/200.

39. A method as defined in claim 38, wherein the third ratio is in the range of 1/20 to 1/100.

40. A method as defined in claim 1, wherein the first mixture in the first reaction zone undergoes a conversion to oxidation products in the range of 5–90%.

41. A method as defined in claim 39, wherein the first mixture in the first reaction zone undergoes a conversion to oxidation products in the range of 10–80%.

42. A method as defined in claim 40, wherein the first mixture in the first reaction zone undergoes a conversion to oxidation products in the range of 20–60%.

43. A method as defined in claim 7, wherein the third ratio is in the range of 1/20 to 1/100, and wherein the first mixture in the first reaction zone undergoes a conversion to oxidation products in the range of 20–60%.

44. A method as defined in claim 8, wherein the third ratio is in the range of 1/20 to 1/100, and wherein the first mixture in the first reaction zone undergoes a conversion to oxidation products in the range of 20–60%.

45. A method as defined in claim 9, wherein the third ratio is in the range of 1/20 to 1/100, and wherein the first mixture in the first reaction zone undergoes a conversion to oxidation products in the range of 20–60%.

46. A method as defined in claim 17, wherein the third ratio is in the range of 1/20 to 1/100, and wherein the first mixture in the first reaction zone undergoes a conversion to oxidation products in the range of 20–60%.

* * * * *